(12) United States Patent
Mihailescu et al.

(10) Patent No.: US 12,239,301 B2
(45) Date of Patent: Mar. 4, 2025

(54) METHODS AND SYSTEMS FOR LOCALIZATION OF TARGETS INSIDE A BODY

(71) Applicant: Ziteo, Inc., Pleasant Hill, CA (US)

(72) Inventors: Lucian Mihailescu, Pleasant Hill, CA (US); Michael J. Quinlan, Pleasant Hill, CA (US); Victor Arie Negut, Berkeley, CA (US)

(73) Assignee: Ziteo, Inc., Pleasant Hill, CA (US)

( * ) Notice: Subject to any disclaimer, the term of this patent is extended or adjusted under 35 U.S.C. 154(b) by 365 days.

(21) Appl. No.: 17/930,532

(22) Filed: Sep. 8, 2022

(65) Prior Publication Data

US 2023/0028501 A1  Jan. 26, 2023

Related U.S. Application Data

(60) Continuation of application No. 16/800,651, filed on Feb. 25, 2020, now Pat. No. 11,464,503, which is a
(Continued)

(51) Int. Cl.
*A61B 34/00* (2016.01)
*A61B 6/00* (2006.01)
(Continued)

(52) U.S. Cl.
CPC ........ *A61B 17/00234* (2013.01); *A61B 6/027* (2013.01); *A61B 6/4057* (2013.01); *A61B 6/4241* (2013.01); *A61B 6/4258* (2013.01); *A61B 6/466* (2013.01); *A61B 6/5205* (2013.01); *A61B 6/547* (2013.01); *A61B 34/20* (2016.02);
(Continued)

(58) Field of Classification Search
None
See application file for complete search history.

(56) References Cited

U.S. PATENT DOCUMENTS

| | | |
|---|---|---|
| 5,436,958 A | 7/1995 | Taylor |
| 5,453,686 A | 9/1995 | Anderson |

(Continued)

FOREIGN PATENT DOCUMENTS

| | | |
|---|---|---|
| CN | 1390335 A | 1/2003 |
| CN | 1792342 A | 6/2006 |

(Continued)

OTHER PUBLICATIONS

Esposito, Marco, et al., "Multimodal US-gamma imaging using collaborative robotics for cancer staging biopsies", International Journal of Computer Assisted Radiology and Surgery, Springer, DE, vol. 11, No. 9, Aug. 9, 2016 (Aug. 9, 2016), pp. 1561-1571.
(Continued)

*Primary Examiner* — Paul A D'Agostino
(74) *Attorney, Agent, or Firm* — Fortem IP LLP

(57) ABSTRACT

The present disclosure relates, in part, to a scanning sufficiency apparatus that computes whether a handheld scanning device has scanned a volume for a sufficiently long time for there to be detections and then indicate to the user that the time is sufficient in 3-D rendered voxels. Also described is a hand held medical navigation apparatus with system and methods to map targets inside a patient's body.

21 Claims, 8 Drawing Sheets

Related U.S. Application Data division of application No. 14/940,040, filed on Nov. 12, 2015, now Pat. No. 10,617,401.

(60) Provisional application No. 62/080,184, filed on Nov. 14, 2014.

(51) Int. Cl.
| | |
|---|---|
| A61B 6/02 | (2006.01) |
| A61B 6/40 | (2024.01) |
| A61B 6/42 | (2024.01) |
| A61B 6/46 | (2024.01) |
| A61B 17/00 | (2006.01) |
| A61B 34/20 | (2016.01) |
| A61B 90/00 | (2016.01) |
| A61B 90/30 | (2016.01) |

(52) U.S. Cl.
CPC ........... *A61B 2034/2048* (2016.02); *A61B 2034/2051* (2016.02); *A61B 2034/2057* (2016.02); *A61B 2034/2065* (2016.02); *A61B 34/25* (2016.02); *A61B 2090/306* (2016.02); *A61B 2090/367* (2016.02); *A61B 2090/3912* (2016.02); *A61B 2090/3937* (2016.02)

(56) References Cited

U.S. PATENT DOCUMENTS

| | | | |
|---|---|---|---|
| 5,786,597 A | 7/1998 | Lingren et al. | |
| 5,891,034 A | 4/1999 | Bucholz | |
| 6,017,779 A * | 1/2000 | Miyasaka | H01L 21/0237 |
| | | | 438/149 |
| 6,031,941 A | 2/2000 | Yano et al. | |
| 6,050,943 A | 4/2000 | Slayton et al. | |
| 6,100,531 A | 8/2000 | Hines et al. | |
| 6,167,296 A | 12/2000 | Shahidi | |
| 6,216,029 B1 | 4/2001 | Paltieli | |
| 6,241,670 B1 | 6/2001 | Nambu | |
| 6,353,227 B1 | 3/2002 | Boxen | |
| 6,381,488 B1 | 4/2002 | Dickey et al. | |
| 6,389,108 B1 | 5/2002 | Ein-Gal | |
| 6,390,982 B1 | 5/2002 | Bova et al. | |
| 6,392,235 B1 | 5/2002 | Barrett et al. | |
| 6,405,072 B1 | 6/2002 | Cosman | |
| 6,491,632 B1 | 12/2002 | Taylor | |
| 6,540,679 B2 | 4/2003 | Slayton et al. | |
| 6,628,984 B2 | 9/2003 | Weinberg | |
| 6,754,596 B2 | 6/2004 | Ashe | |
| 6,891,518 B2 | 5/2005 | Sauer et al. | |
| 6,906,330 B2 | 6/2005 | Blevis et al. | |
| 7,023,962 B2 | 4/2006 | Xu et al. | |
| 7,035,897 B1 | 4/2006 | Devereaux et al. | |
| 7,038,205 B2 | 5/2006 | Bushberg et al. | |
| 7,102,138 B2 | 9/2006 | Belvis et al. | |
| 7,142,905 B2 | 11/2006 | Slayton et al. | |
| 7,166,846 B2 | 1/2007 | Engdahl et al. | |
| 7,199,371 B2 | 4/2007 | Schramm et al. | |
| 7,230,246 B2 | 6/2007 | Hawman | |
| 7,250,607 B1 | 7/2007 | Keck et al. | |
| 7,292,251 B1 | 11/2007 | Gu et al. | |
| 7,345,282 B2 | 3/2008 | Hawman | |
| 7,439,514 B1 | 10/2008 | Uribe et al. | |
| 7,500,795 B2 | 3/2009 | Sandhu | |
| 7,521,681 B2 | 4/2009 | Hawman | |
| 7,549,961 B1 | 6/2009 | Hwang | |
| 7,579,600 B2 | 8/2009 | Joung | |
| 7,596,209 B2 | 9/2009 | Perkins | |
| 7,606,861 B2 | 10/2009 | Killcommons et al. | |
| 7,612,343 B2 | 11/2009 | Vickers | |
| 7,652,259 B2 | 1/2010 | Kimchy et al. | |
| 7,671,340 B2 | 3/2010 | Uribe et al. | |
| 7,723,690 B2 | 5/2010 | Uribe et al. | |
| 7,786,444 B2 | 8/2010 | Wagenaar et al. | |
| 7,809,194 B2 | 10/2010 | Zhang et al. | |
| 7,831,024 B2 | 11/2010 | Metzler et al. | |
| 7,835,785 B2 | 11/2010 | Scully et al. | |
| 7,894,078 B2 | 2/2011 | Gharib et al. | |
| 7,912,733 B2 | 3/2011 | Clements et al. | |
| 7,914,453 B2 | 3/2011 | Slayton et al. | |
| 7,989,771 B2 | 8/2011 | Wieczorek et al. | |
| 8,000,773 B2 | 8/2011 | Rousso et al. | |
| RE42,952 E | 11/2011 | Hu et al. | |
| 8,060,185 B2 | 11/2011 | Hunter et al. | |
| 8,067,741 B2 | 11/2011 | Beekman | |
| 8,090,429 B2 | 1/2012 | Vija et al. | |
| 8,109,878 B1 | 2/2012 | Oruanaidh et al. | |
| 8,153,986 B2 | 4/2012 | Mihailescu et al. | |
| 8,195,417 B2 | 6/2012 | Feiweier et al. | |
| 8,235,909 B2 | 8/2012 | Barthe et al. | |
| 8,423,125 B2 | 4/2013 | Rousso et al. | |
| 8,445,851 B2 | 5/2013 | Rousso et al. | |
| 8,476,610 B2 | 7/2013 | Hawman et al. | |
| 8,487,265 B2 | 7/2013 | Heukensfeldt et al. | |
| 8,552,389 B2 | 10/2013 | Jansen et al. | |
| 8,565,860 B2 | 10/2013 | Kimchy et al. | |
| 8,594,769 B2 | 11/2013 | Mostafavi | |
| 8,748,827 B2 | 6/2014 | Zilberstein et al. | |
| 8,831,708 B2 | 9/2014 | Paladini | |
| 9,014,340 B2 | 4/2015 | Kurochi | |
| 9,040,925 B2 | 5/2015 | Giarmana et al. | |
| 9,119,669 B2 | 9/2015 | Keglovich et al. | |
| 9,129,422 B2 | 9/2015 | Mountney et al. | |
| 9,146,198 B2 | 9/2015 | Wendler et al. | |
| 9,263,160 B2 | 2/2016 | Kang et al. | |
| 9,286,732 B2 | 3/2016 | Wendler | |
| 9,344,700 B2 | 5/2016 | Zalevsky et al. | |
| 9,345,441 B2 | 5/2016 | Wendler | |
| 9,561,019 B2 | 2/2017 | Mihailescu et al. | |
| 9,566,454 B2 | 2/2017 | Barthe et al. | |
| 9,711,251 B2 | 7/2017 | Lee et al. | |
| 9,743,898 B2 | 8/2017 | Wendler et al. | |
| 9,903,962 B2 | 2/2018 | Kovalski et al. | |
| 10,033,996 B2 | 7/2018 | Zalevsky et al. | |
| 10,148,676 B2 * | 12/2018 | Wang | H04L 63/1416 |
| 10,219,782 B2 | 3/2019 | Pandey et al. | |
| 10,426,350 B2 | 10/2019 | Mihailescu et al. | |
| 10,617,366 B2 | 4/2020 | Feng et al. | |
| 10,617,401 B2 | 4/2020 | Mihailescu et al. | |
| 10,795,036 B2 | 10/2020 | Boardman et al. | |
| 10,869,611 B2 | 12/2020 | Ernst et al. | |
| 11,439,192 B2 | 9/2022 | Bock | |
| 11,439,358 B2 | 9/2022 | Quinlan et al. | |
| 11,678,804 B2 | 6/2023 | Mihailescu et al. | |
| 11,883,214 B2 | 1/2024 | Quinlan et al. | |
| 2001/0056234 A1 | 12/2001 | Weinberg | |
| 2002/0052709 A1 | 5/2002 | Akatsuka et al. | |
| 2002/0077543 A1 * | 6/2002 | Grzeszczuk | A61B 90/36 |
| | | | 348/E13.008 |
| 2002/0087080 A1 | 7/2002 | Slayton et al. | |
| 2003/0004413 A1 | 1/2003 | Inoue et al. | |
| 2003/0047597 A1 | 3/2003 | Knowles et al. | |
| 2003/0112922 A1 | 6/2003 | Burdette et al. | |
| 2003/0128801 A1 | 7/2003 | Eisenberg et al. | |
| 2003/0194050 A1 | 10/2003 | Eberhard et al. | |
| 2003/0208117 A1 | 11/2003 | Shwartz et al. | |
| 2004/0054248 A1 * | 3/2004 | Kimchy | A61B 5/06 |
| | | | 600/3 |
| 2004/0152975 A1 | 8/2004 | Blevis | |
| 2004/0204646 A1 | 10/2004 | Nagler et al. | |
| 2005/0104881 A1 | 5/2005 | Yoshida et al. | |
| 2005/0256406 A1 | 11/2005 | Barthe et al. | |
| 2005/0271300 A1 | 12/2005 | Pina | |
| 2005/0285844 A1 | 12/2005 | Morita et al. | |
| 2005/0289472 A1 | 12/2005 | Morita et al. | |
| 2006/0079764 A1 | 4/2006 | Wright et al. | |
| 2006/0100509 A1 | 5/2006 | Wright et al. | |
| 2006/0106306 A1 * | 5/2006 | Essner | A61B 8/0833 |
| | | | 600/407 |
| 2006/0122617 A1 | 6/2006 | Lavallee et al. | |
| 2006/0237652 A1 | 10/2006 | Kimchy et al. | |
| 2007/0015987 A1 | 1/2007 | Benlloch et al. | |
| 2007/0078334 A1 | 4/2007 | Scully et al. | |
| 2007/0135984 A1 | 6/2007 | Breed et al. | |

(56) References Cited

U.S. PATENT DOCUMENTS

| | | |
|---|---|---|
| 2007/0161884 A1 | 7/2007 | Black et al. |
| 2007/0167712 A1 | 7/2007 | Keglovich et al. |
| 2007/0205373 A1 | 9/2007 | Kornblau et al. |
| 2007/0223651 A1 | 9/2007 | Wagenaar et al. |
| 2007/0225553 A1 | 9/2007 | Shahidi |
| 2007/0236514 A1 | 10/2007 | Agusanto et al. |
| 2008/0042067 A1 | 2/2008 | Rousso et al. |
| 2008/0051651 A1 | 2/2008 | Yamamoto et al. |
| 2008/0073543 A1 | 3/2008 | Vija et al. |
| 2008/0078937 A1* | 4/2008 | Tsuchiya ............... G01T 1/2928 250/366 |
| 2008/0084961 A1 | 4/2008 | Keppel et al. |
| 2008/0086059 A1 | 4/2008 | Keppel et al. |
| 2008/0128626 A1 | 6/2008 | Rousso et al. |
| 2009/0018403 A1 | 1/2009 | Black et al. |
| 2009/0078875 A1 | 3/2009 | Rousso et al. |
| 2009/0152471 A1 | 6/2009 | Rousso et al. |
| 2009/0209852 A1 | 8/2009 | Mate et al. |
| 2009/0259123 A1 | 10/2009 | Navab et al. |
| 2009/0306509 A1 | 12/2009 | Pedersen et al. |
| 2010/0016765 A1 | 1/2010 | Hall et al. |
| 2010/0183213 A1 | 7/2010 | Keppel et al. |
| 2010/0187425 A1 | 7/2010 | Majewski et al. |
| 2010/0198068 A1 | 8/2010 | Rivaz et al. |
| 2010/0266171 A1* | 10/2010 | Wendler ............... A61B 6/5205 382/128 |
| 2010/0268067 A1 | 10/2010 | Razzaque et al. |
| 2010/0268070 A1 | 10/2010 | Jaffer et al. |
| 2010/0298704 A1 | 11/2010 | Pelissier et al. |
| 2011/0007959 A1 | 1/2011 | Schulz et al. |
| 2011/0046483 A1 | 2/2011 | Fuchs et al. |
| 2011/0098083 A1 | 4/2011 | Lablans |
| 2011/0137156 A1 | 6/2011 | Razzaque et al. |
| 2011/0144451 A1 | 6/2011 | Robertson |
| 2011/0178373 A1 | 7/2011 | Pacey et al. |
| 2011/0237945 A1 | 9/2011 | Foroughi et al. |
| 2011/0306025 A1 | 12/2011 | Sheehan et al. |
| 2012/0032086 A1* | 2/2012 | Daghighian ............ G01T 1/161 250/363.02 |
| 2012/0035462 A1 | 2/2012 | Maurer et al. |
| 2012/0069167 A1 | 3/2012 | Liu et al. |
| 2012/0128223 A1 | 5/2012 | Rivaz et al. |
| 2012/0172699 A1* | 7/2012 | Nagler ............... A61B 6/4266 600/407 |
| 2012/0226150 A1 | 9/2012 | Balicki et al. |
| 2012/0253200 A1 | 10/2012 | Stolka et al. |
| 2012/0305812 A1 | 12/2012 | Bowen et al. |
| 2013/0020493 A1 | 1/2013 | Ishii et al. |
| 2013/0136302 A1 | 5/2013 | Nam et al. |
| 2013/0158389 A1 | 6/2013 | Oconnor |
| 2013/0168570 A1 | 7/2013 | Wendler et al. |
| 2013/0172739 A1 | 7/2013 | Paladini |
| 2013/0229529 A1 | 9/2013 | Lablans |
| 2013/0237811 A1 | 9/2013 | Mihailescu et al. |
| 2013/0261446 A1* | 10/2013 | Paladini ............... A61B 6/5223 600/436 |
| 2013/0338490 A1 | 12/2013 | Wendler |
| 2014/0042326 A1 | 2/2014 | Miyaoka et al. |
| 2014/0142424 A1 | 5/2014 | Lall et al. |
| 2014/0151563 A1 | 6/2014 | Rousso et al. |
| 2014/0163368 A1 | 6/2014 | Rousso et al. |
| 2014/0175291 A1 | 6/2014 | Giarmana et al. |
| 2014/0218720 A1 | 8/2014 | Kindem |
| 2014/0235921 A1 | 8/2014 | Wendler et al. |
| 2014/0241600 A1 | 8/2014 | Mountney et al. |
| 2014/0249402 A1 | 9/2014 | Kimchy et al. |
| 2014/0343344 A1 | 11/2014 | Saunders et al. |
| 2014/0350392 A1 | 11/2014 | Lundqvist et al. |
| 2014/0369560 A1 | 12/2014 | Wendler |
| 2015/0065875 A1 | 3/2015 | Friebe |
| 2015/0150525 A1 | 6/2015 | Navab et al. |
| 2015/0238167 A1 | 8/2015 | Lall et al. |
| 2015/0305700 A1 | 10/2015 | Wendler et al. |
| 2016/0073976 A1 | 3/2016 | Moriyasu |
| 2016/0135762 A1 | 5/2016 | Mihailescu et al. |
| 2016/0242744 A1 | 8/2016 | Mihailescu et al. |
| 2016/0253826 A9 | 9/2016 | Ziv et al. |
| 2016/0282432 A1 | 9/2016 | Wang |
| 2016/0287211 A1 | 10/2016 | Dacosta et al. |
| 2017/0112577 A1 | 4/2017 | Bonutti et al. |
| 2019/0000318 A1 | 1/2019 | Caluser |
| 2019/0336004 A1* | 11/2019 | Mihailescu ........... A61B 6/4417 |
| 2020/0146641 A1 | 5/2020 | Mu |
| 2020/0237321 A1 | 7/2020 | Feng et al. |
| 2022/0087624 A1 | 3/2022 | Quinlan et al. |
| 2023/0028501 A1 | 1/2023 | Mihailescu et al. |
| 2023/0030008 A1 | 2/2023 | Quinlan et al. |
| 2023/0389801 A1 | 12/2023 | Mihailescu et al. |

FOREIGN PATENT DOCUMENTS

| | | |
|---|---|---|
| CN | 1805711 A | 7/2006 |
| CN | 101219061 A | 7/2008 |
| CN | 101561831 A | 10/2009 |
| CN | 101645170 A | 2/2010 |
| CN | 101719221 A | 6/2010 |
| CN | 101952837 A | 1/2011 |
| CN | 102258399 A | 11/2011 |
| CN | 102378594 A | 3/2012 |
| CN | 104271046 A | 1/2015 |
| CN | 106659474 A | 5/2017 |
| CN | 104271046 B | 1/2018 |
| CN | 105708484 B | 8/2018 |
| CN | 108095761 B | 10/2021 |
| DE | 10210648 A1 | 10/2003 |
| DE | 102008034579 A1 | 2/2010 |
| EP | 1795142 A1 | 6/2007 |
| EP | 2001389 A2 | 12/2008 |
| EP | 1554987 B1 | 3/2009 |
| EP | 1269916 B1 | 3/2011 |
| EP | 1439780 B1 | 3/2011 |
| EP | 2584957 A1 | 5/2013 |
| EP | 2045626 B1 | 6/2013 |
| EP | 2606825 A1 | 6/2013 |
| EP | 2482101 B1 | 1/2014 |
| EP | 2310876 B1 | 3/2014 |
| EP | 2024761 B1 | 5/2014 |
| EP | 2165215 B1 | 5/2014 |
| EP | 2746815 A1 | 6/2014 |
| EP | 2755556 A1 | 7/2014 |
| EP | 2758131 A1 | 7/2014 |
| EP | 2822472 A1 | 1/2015 |
| EP | 2853223 A1 | 4/2015 |
| EP | 2073039 B1 | 8/2015 |
| EP | 2922471 A1 | 9/2015 |
| EP | 1554987 B2 | 12/2015 |
| EP | 2347285 B1 | 1/2019 |
| EP | 2949272 B1 | 3/2019 |
| EP | 3952747 A4 | 12/2022 |
| JP | 60170779 A | 9/1985 |
| JP | 10148676 A | 6/1998 |
| JP | 2000245733 A | 9/2000 |
| JP | 2003000594 A | 1/2003 |
| JP | 2004512502 A | 4/2004 |
| JP | 2007282792 A | 11/2007 |
| JP | 2008089341 A | 4/2008 |
| JP | 2010510490 A | 4/2010 |
| JP | 2010200894 A | 9/2010 |
| JP | 2014530348 A | 11/2014 |
| NL | 2022634 B1 | 9/2020 |
| WO | 2002016965 A3 | 2/2002 |
| WO | 0179884 A9 | 12/2002 |
| WO | 2004019799 A2 | 3/2004 |
| WO | 2006127142 A2 | 11/2006 |
| WO | 2007111570 A2 | 10/2007 |
| WO | 2007131561 A2 | 11/2007 |
| WO | 2008063835 A3 | 11/2008 |
| WO | 2011063266 A2 | 5/2011 |
| WO | 2011161197 A1 | 12/2011 |
| WO | 2013038011 A1 | 3/2013 |
| WO | 2013041720 A1 | 3/2013 |
| WO | 2013134559 A1 | 9/2013 |
| WO | 2014080013 A1 | 5/2014 |

(56) References Cited

FOREIGN PATENT DOCUMENTS

| | | |
|---|---|---|
| WO | 2017083611 A1 | 5/2017 |
| WO | 2020175985 A1 | 9/2020 |
| WO | 2020210532 A1 | 10/2020 |

OTHER PUBLICATIONS

Lees et al., "A Hybrid Camera for simultaneous imaging of gamma and optical photons", Journal of Instrumentation, Institute of Physics Publishing, Bristol, GB, vol. 7, No. 6,Jun. 18, 2012 (Jun. 18, 2012), p. P06009.
Kaissas, I. et al., 3-D Localization of Gamma Ray Sources with Coded Apertures for Medical Applications, Journal of Physics: Conference Series, 637 (2015), 5 pages.
Laurent, P. et al., Collimators, Coded Masks and all Sky Monitors, Escole Astroparticules, 2016, 34 pages.
Moore, Richard H. et al, A Variable Angle Slant-Hole Collimator, The Journal of Nuclear Medicine, vol. 24, No. 1, 1983, pp. 61-65.
Ansar, et al., "Linear Pose Estimation from Points of Lines", IEEE Transactions on Pattern Analysis and Machine Intelligence, May 2003, vol. 25(5), pp. 578-589.
Chiao, et al., "Ocular Examination for Trauma; Clinical Ultrasound Aboard the International Space Station", The Journal of Trauma Injury, Infection and Critical Care, 2005, vol. 58(5), pp. 885-889.
De Cunha, et al., "The MIDSTEP System for Ultrasound guided Remote Telesurgery", Proceeding of the 20th Annual International Conference of the IEEE Engineering in Medicine and Biology Society, 1998, vol. 20(3), pp. 1266-1269.
Fofi, et al., "A comparative survey on invisible structured light", Proc. SPIE5303, Machine Vision Applications in Industrial Inspection XII, 90, May 2004, doi: 10.1117/12.525369; http:/dx.doi.org/ 10.1117/12.52536.
Gat, "Imagining Spectroscopy Using Tunable Filters: A Review", Proc. SPIE, vol. 4056, Wavelet Applications VII, 50, Apr. 5, 2000, pp. 50-64.
Gee et al., "Sensorless freehand 3D ultrasound in real tissue: Speckle decorrelation without fully developed speckle", Medical Image Analysis, 10, 2006, 137-149.
Gibon et al., "Stereotactic Localization in Medical Imaging: A Technical and Methodological Review", Journal of Radiosurgery, 1999, vol. 2(3), pp. 167-180.
Goldsmith, "An Inertial-Optical Tracking System for Quantitative, Freehand, 3D Ultrasound", (thesis) Worcester Polytechnic Institute, Dec. 2008, 289 pages.
Goldsmith et al., "An Inertial-Optical Tracking System for Portable, Quantitative, 3D Ultrasound", IEEE International Ultrasonics Symposium Proceedings, 2008, pp. 45-49, doi: 10.1109/ULTSYM. 2008.0012.
Hansard et al., "Time-of-Flight, Principles, Methods and Applications, Springer Briefs in Computer Science", Springer Publications, Nov. 2012, 102 pages.
Kalman, "A New Approach to Linear Filtering and Prediction Problems", Journal of Basic Engineering, 82 (Series D): 35-45, 12 pages.
Lagrone et al., "A review of training opportunities for ultrasonography in low and middle income countries", Tropical Medicine and International Health, Jul. 2012, vol. 17(7), pp. 808-819.
Lepetit et al., "An Accurate O(n) Solution to the PnP Problem", International Journal of Computer Vision, 2009; vol. 81, pp. 155-166.
Lepetit et al., "EPnP: Accurate Non-Iterative O(n) Solution to the PnP Problem", Available Online at: https://upcommons.upc.edu/ bitstream/handle/2117/10327/moreno_ijcv2009%20.pdf?sequence= 1, Feb. 18, 2009, 22 pages.
Lu et al., "Fast and Globally Convergent Pose Estimation From Video Images", Feb. 18, 1998, 26 pages.
Mercier et al., "A Review of Calibration Techniques for Freehand 3-D Ultrasound Systems", Ultrasound in Med. & Biol., 2005, vol. 31(2), pp. 143-165, doi:10.1016/j.ultrasmedbio.2004.11.001.
Mercier et al., "New prototype neuronavigation system based on preoperative imaging and intraoperative freehand ultrasound: system description and validation", Int. J. Cars, 2011, 6:507-522, doi:10.1007/s11548-010-0535-3.
Mikulik et al., "Telemedicine-Guided Carotid and Transcranial Ultrasound: A Pilot Feasibility Study", Stroke, 2006, pp. 229-230, doi: 10.1161/0.1str.0000196988.45318.97, Downloaded from http:// stroke.ahajournals.org/ at Lawrence Berkeley Lab on Jun. 30, 2012.
Mordohai et al., "Real-Time Video-Based Reconstruction of Urban Environments", University of North Carolina, Chapel Hill, NC, USA, 2007, 8 pages.
Nevatia et al., "Computer Aided Medical Diagnosis and Surgery System: Towards Automated Medical Diagnosis for Long Term Space Missions", 7 pages.
Ng et al., "Light Field Photography with a Hand-held Plenoptic Camera", Stanford Tech Report CTSR 2005-02, Apr. 2005, 11 pages.
Odell et al., "Next Generation, High Accuracy Optical Tracker for Target Acquisition and Cueing", 2006, 10 pages.
Prager et al., "Three-dimensional ultrasound imaging", Proc. IMechE, 2009, vol. 224 Part H: J. Engineering in Medicine, pp. 193-223.
Rafii-Tari, "Panorama Ultrasound for Navigation and Guidance of Epidural Anesthesia", A Thesis submitted in partial fulliment of the requirements for the degree of Master of Applied Science, The University of British Columbia, Vancouver, Sep. 2011, 99 pages.
Ren et al., "SAD based Sensor-less Freehand 3D Ultrasound Reconstruction with Adaptive Curve Correction", 2010, 10.1109/ ICBBE.2010.5516742.
Sansoni et al., "State-of-the-Art and Application of 3D Imaging Sensors in Industry, Cultural Heritage, Medicine, and Criminal Investigation", Sensors, 2009, vol. 9, pp. 568-601.
Schneider et al., "Development and Testing of a New Magnetic-Tracking Device for Image Guidance", Proc. SPIE 6509, Medical Imaging, 2007: Visualization and Image-Guided Procedures, 650901, Mar. 21, 2007; doi:10.1117/12.713249.
Sheehan et al., "Expert visual guidance of ultrasound for telemedicine", J Telemed Telecare, 2010, 16(2): 77-82.
Sheehan et al., "Tracking Three Dimensional Ultrasound with Immunity from Ferro-Magnetic Interference", LNCS, 2003, 2879, pp. 192-198.
Stolka et al., "Navigation with Local Sensors in Handheld 3D Ultrasound Initial in-vivo Experience", Proc. of SPIE, vol. 7968 79681J-1, downloaded from http://proceedings.spiedigitallibrary. org on Dec. 12, 2012, 9 pages.
Suenaga et al., "A Tele-instruction system for ultrasound probe operation based on shared AR technology", 2001 Conference Proceedings of the 23rd Annual International Conference of the IEEE Engineering in Medicine and Biology Society, 2001, 5 pages.
Takacs et al., "A Portable Ultrasound Guidance and Training System Using High Fidelity Virtual Human Models", Proceeding of the International Conference on Medical Information Visualization— MediVis'06, 2006, 5 pages.
Takacs et al., "Compact Anatomically Guided Ultrasound for Casualty Care", First International Conference on Advances in Computer-Human Interaction, IEEE, 2008, pp. 120-123.
Wang et al., "The Kinect as an interventional tracking system", Proc. of SPIE, vol. 8316 83160U-1, downloaded from http:// spiedigitallibrary.org on Dec. 12, 2012.
Xiao-Shan et al., "Complete solution classification for the perspective-three-point problem", Pattern Analysis and Machine Intelligence, Aug. 2003, vol. 25, No. 8, pp. 930-942, IEEE Transactions on 2003:25:930-43.
Yu et al., "A 3D Freehand Ultrasound System for Multi-view Reconstructions from Sparse 2D Scanning Planes", BioMedical Engineering OnLine, 2011, 10:7, 22 pages.
Zhao et al., "Improved 3D Reconstruction Algorithm for Ultrasound B-scan Image with Freehand Tracker", Proceedings of SPIE, vol. 7629, Mar. 12, 2010, pp. 762914-1-762914-12.

\* cited by examiner

METHODS AND SYSTEMS FOR LOCALIZATION OF TARGETS INSIDE A BODY

CROSS-REFERENCES TO RELATED APPLICATIONS

This application is a continuation of U.S. patent application Ser. No. 16/800,651, filed Feb. 25, 2020, which is a divisional of U.S. patent application Ser. No. 14/940,040, filed Nov. 12, 2015, now U.S. Pat. No. 10,617,401 and U.S. Provisional Patent Application No. 62/080,184, filed Nov. 14, 2014, the teachings of which are hereby incorporated by reference in their entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

Generally, embodiments of the present application relate to apparatuses used in image guided surgery techniques. Specifically, this application relates to medical imaging instruments and the use of data from detectors taken pre- and intra-operatively to guide medical procedures. Such procedures include tissue excision, tissue biopsy, injections, simulations or implantations.

Image guided surgery apparatuses are used to assist surgeons performing medical procedures. These apparatuses generally use tracked surgical instruments in conjunction with pre-operative and intra-operative image datasets with the purpose of representing the position and orientation of the surgical instruments in respect to the adjacent anatomy.

Some existing tracking instruments use overhead optical stereoscopic systems in conjunction with infrared reflective spheres attached to instruments and patient. Other devices use camera systems attached to the medical imaging systems to track the position and orientation of these medical instruments with respect to other medical instruments, such as needles. The function of these devices often depend on one or more instruments remaining in the line-of-sight of the tracking camera to determine the correct position and orientation of the medical instrument. In the course of a standard procedure, the movement of the surgeon, assisting medical personnel, or of medical instruments and equipment can obstruct the line of sight of the tracking camera, resulting in poor tracking and imaging data. Furthermore, overhead optical tracking systems require more equipment inside the room, which can hinder the procedure being performed.

As such, there is a need in the art for more accurate and precise medical navigation devices.

BRIEF SUMMARY

Generally, the embodiments of the present invention relate to a scanning sufficiency device that is able to instantaneously report to a user how well a particular area of a subject's body has been scanned. The devices described herein improve scanning quality and reduce errors by better defining the precise location of a detected signal.

Embodiments can also relate to hand held medical navigation apparatuses with systems and methods to map targets inside the body. The apparatuses described herein use tracking systems, such as cameras, attached to medical sensing instruments to track the position of the medical sensing instruments with respect to the patient. The apparatus sometimes has a tracking system with a lateral view.

The images captured by the tracking camera or scanning data from a medical sensing instrument can be presented to the operator on a screen, on a head mounted display, or using other visualization device such as projectors. Data sets collected by the tracking camera and the medical sensing instrument can also be combined to create an overlaid model that can be presented on the above mentioned visualization means. Various aspects of the information collected by the apparatuses can be presented in a graphical user interface that can improve the quality of a scan.

In some embodiments, the present invention relates to a scanning sufficiency apparatus. The scanning sufficiency apparatus includes, an ionizing radiation sensor within a housing assembly, a tracking system providing the position and orientation of the sensor with respect to an examined object, a visualization device operably linked to the at least one processor to show an instantaneous image, at least one processor and a memory operatively coupled with the sensor and the tracking system, the memory having instructions for execution by the at least one processor configured to associate scanning data from the sensor with the calculated spatial position and orientation of the sensor with respect to the object to create registered scans, separate an adjacent volumetric space into 3-D imaging elements, produce a 3-D model of radioactive sources by combining the registered scans, calculate a scanning completeness of a particular 3-D imaging element by calculating a scanning completeness value (SCV), create a map of SCV values, and create the instantaneous image comprising a rendering of the SCV map, wherein the calculation of the SCV takes into consideration the sensor tracking information to inform the user about the partial volumes that have been scanned enough and the partial volumes that have not been scanned enough for a pre-defined scanning objective.

In some embodiments, the present invention also includes an image formation and navigation apparatus. The image formation and navigation apparatus includes, a housing assembly, an ionizing radiation sensor at least partially enclosed within the housing assembly and disposed towards the distal end of the housing assembly, an optical camera at least partially enclosed within the housing assembly, the tracking camera having a field of view that overlaps partially with the field of view of the sensor; a visualization device operably linked to at least one processor and configured to show instantaneous renderings of images, the at least one processor operatively coupled with a memory, the sensor and the camera, the memory having instructions for execution by the at least one processor configured to determine a pose of the camera with respect to an object using an image captured by the camera and, using transformations derived from the camera being rigidly connected with the sensor, determine a spatial position and orientation of the sensor with respect to the object, associate scanning data from the sensor with the calculated spatial position and orientation of the sensor with respect to the object to create registered scans, create a 3-D map of sources generating signatures measured by the sensor by using at least two registered scans, create an image for visualization on the visualization device which is a combination of a rendered image of the 3-D map and an image processed from an image captured by the camera, create and send for visualization on the visualization device renderings of 1-D and 2-D projections of the 3-D map along or perpendicular to the housing assembly preferred axis.

In some embodiments, the present invention provides a laparoscopic or intra-cavity image formation and navigation apparatus, comprising a housing assembly having an elongated, essentially cylindrical part with a diameter of less than 30 mm, a gamma ray sensor with spectroscopic and position resolution at least partially enclosed within the elongated part of the housing assembly, towards the distal end of the elongated part, a tracking and co-registration system to track the position and orientation of the sensor and the camera with respect to examined organs, an optical camera at least partially enclosed within another housing assembly having an elongated, essentially cylindrical part with a diameter of less than 30 mm, towards the distal end of the elongated part, the tracking camera having a field of view that observes the general area where the sensor is operated, the at least one processor operatively coupled with a memory, the sensor, the tracking and co-registration system, and the camera, the memory having instructions for execution by the at least one processor configured to associate gamma ray interaction data from the sensor with the calculated spatial position and orientation of the sensor with respect to the object to create registered scans, determine a scattering angle around a scattering direction of a gamma ray interacting at least two times in the sensor system by resolving the kinematics of the gamma ray interactions within the sensor system, create a 3-D map of gamma ray sources by resolving statistically the intersection of at least two spatially registered cones formed by the determined scattering angle around the scattering direction.

In some embodiments the present invention relates to a radiation position sensitive apparatus. The radiation position sensitive apparatus includes an elongated housing assembly having a longitudinal axis, a gamma ray probe at least partially enclosed within the elongated housing assembly and disposed along the longitudinal axis of the elongated housing assembly, a tracking camera at least partially enclosed within the elongated housing assembly, the tracking camera having a tracking field of view that is lateral to the longitudinal axis, the tracking camera disposed at a predetermined proximity to the gamma ray probe, at least one processor and a memory operatively coupled with the tracking camera, the memory having instructions for execution by the at least one processor for calculating a spatial position and orientation of lateral images taken by the tracking camera with respect to a fiducial and associating scanning data from the gamma ray probe with the calculated spatial position and orientation of the lateral images to determine a position and orientation of the scanning data using the known proximity of the gamma ray probe to the tracking camera.

The radiation position sensitive apparatus can include a memory that has instructions for execution by the at least one processor configured to convert the scanning data to a reconstructed diagram identifying a relative location of a radiation source to the fiducial. In some embodiments, the reconstructed diagram is produced using Compton imaging, self-collimation effects, and proximity imaging.

The radiation position sensitive apparatus can include a memory that has instructions for execution by the at least one processor configured to combine the lateral images and the reconstructed diagram to produce a three dimensional (3-D) model of a subject's tissue.

The radiation position sensitive apparatus can include a display screen operably linked to the at least one processor and configured to show instantaneous renderings of the 3-D model. The display screen can also be configured to show instantaneous renderings of the reconstructed diagram.

In some embodiments the fiducial marker is a marker with a binary coding applied to an area of interest.

The radiation position sensitive apparatus can include a transparent optical window along a side of the elongated housing through which the tracking camera is configured to see the tracking field of view. The optical window can also include a device configured for supplying a stream of fluid in order to keep the transparent optical window clear. The fluid can include air or liquid.

The radiation position sensitive apparatus can include an illumination source with an illumination field of view that overlaps with the tracking field of view. The illumination source can be an optical fiber.

The radiation position sensitive apparatus can include a transparent illumination window wherein the illumination source illuminates the tracking field of view through the transparent illumination window. The illumination window can also include a device configured for supplying a stream of fluid to keep the transparent illumination window clear. The fluid can be air or liquid.

The illumination source can be spatially patterned light, spectrally coded light, time coded light, uniform light, and combinations thereof.

The gamma ray probe in the radiation position sensitive apparatus can include an enclosed matrix surrounding a sensor. The material of the sensor can be cadmium zinc tellurium (CdZnTe) detector, a position sensitive scintillator, a segmented silicon (Si) detector, a depleted charge-coupled device (CCD) sensor, a depleted complementary metal-oxide semiconductor (CMOS) sensor, or any other known sensor in the art.

The sensor of the gamma ray probe in the radiation position sensitive apparatus includes a first sensor and can include a second sensor proximate to the first sensor.

In another aspect, the present invention includes a medical navigation apparatus including an elongated housing assembly having a longitudinal axis, a sensor probe at least partially enclosed within the elongated housing assembly and disposed along the longitudinal axis of the elongated housing assembly, a tracking camera at least partially enclosed within the elongated housing assembly, the tracking camera pointing outward from the longitudinal axis, the tracking camera disposed at a predetermined position and orientation with respect to the probe, at least one processor and a memory operatively coupled with the tracking camera, the memory having instructions for execution by the at least one processor for calculating a spatial position and orientation of the tracking camera with respect to a fiducial based on an image that includes the fiducial, computing a spatial position and orientation of the sensor probe, and associating scanning data from the probe with the computed spatial position and orientation of the sensor probe.

The sensor prove of the medical navigation apparatus can be a magnetic sensor, an electromagnetic sensor, a gamma ray detector, or any other known sensor useful in the art.

In another aspect, the present invention includes a scanning completeness apparatus including a detector, a tracking camera rigidly attached to the detector and being a known proximity to the detector, at least one processor and a memory operatively coupled with the detector and the tracking camera, the memory having instructions for execution by the at least one processor configured for calculating a spatial position and orientation of images taken by the tracking camera with respect to a fiducial marker, associating scanning data from the detector with the calculated spatial position and orientation of the images to determine a position and orientation of the scanning data using the known proximity of the detector to the tracking camera, producing a three dimensional (3-D) model of a subject's tissue detected by the tracking camera and the relative location of one or more signals detected by the detector, and separating volumetric units of the 3-D model into voxels, wherein scanning completeness of a particular voxel is determined by instantaneously calculating a scanning completeness value (SCV).

The scanning completeness value of the scanning completeness apparatus can be determined by summing the probability that the signal emitted by a marker inside the voxel is detected by the detector at each moment of time over the scanning period.

The scanning completeness apparatus can also include a display screen operably linked to the at least one processor to show an instantaneous image of the 3-D model. The 3-D model can be shown as a 3-D mesh of the patient body. The 3-D model can also include an overlapped view of the scanning data and the images.

In some embodiments, the scanning completeness apparatus includes a notification to the user that the scanning of a particular voxel is sufficient. The indication to the user includes an audible sound, a color change in a voxel, or a conversion of a voxel from opaque to transparent.

In some embodiments the fiducial marker is a marker with a binary coding applied to an area of interest.

The detector of the scanning sufficiency device can be a radiation detector, an electromagnetic sensor, a magnetic sensor, an ultrasound device, or any other detector useful in the art.

The camera of the scanning sufficiency device can include an optical camera. The optical camera can include a visible light camera or an infrared (IR) camera.

DETAILED DESCRIPTION

Generally, medical tracking apparatuses are described herein. Particularly described are exemplary apparatuses used to accurately determine the position of targets of interest inside the body in respect to the body of the patient or a fiducial. For example apparatuses described herein can be used to provide information about critical tissue, such as veins, arteries and nerves, that may be present on the path towards those targets, so that surgical instruments handled by the operator will not damage them. Further uses for the apparatuses described herein include identifying the location of a tissue to be removed, such as a tumor, or to be used post-operatively to determine if the excision of a particular tissue was performed successfully.

Targets of interest inside a subject's body can be labeled by any known signal in the art. Such signals include, but are not limited to, a Tc-99m tracer, a radioactive seed or other radioactive tracer, magnetic nano-particles, micro-bubbles, and fludeoxyglucose (FDG). A person of skill in the art will recognize that different types of detectors are necessary to detect these exemplary signals.

Figure 1:
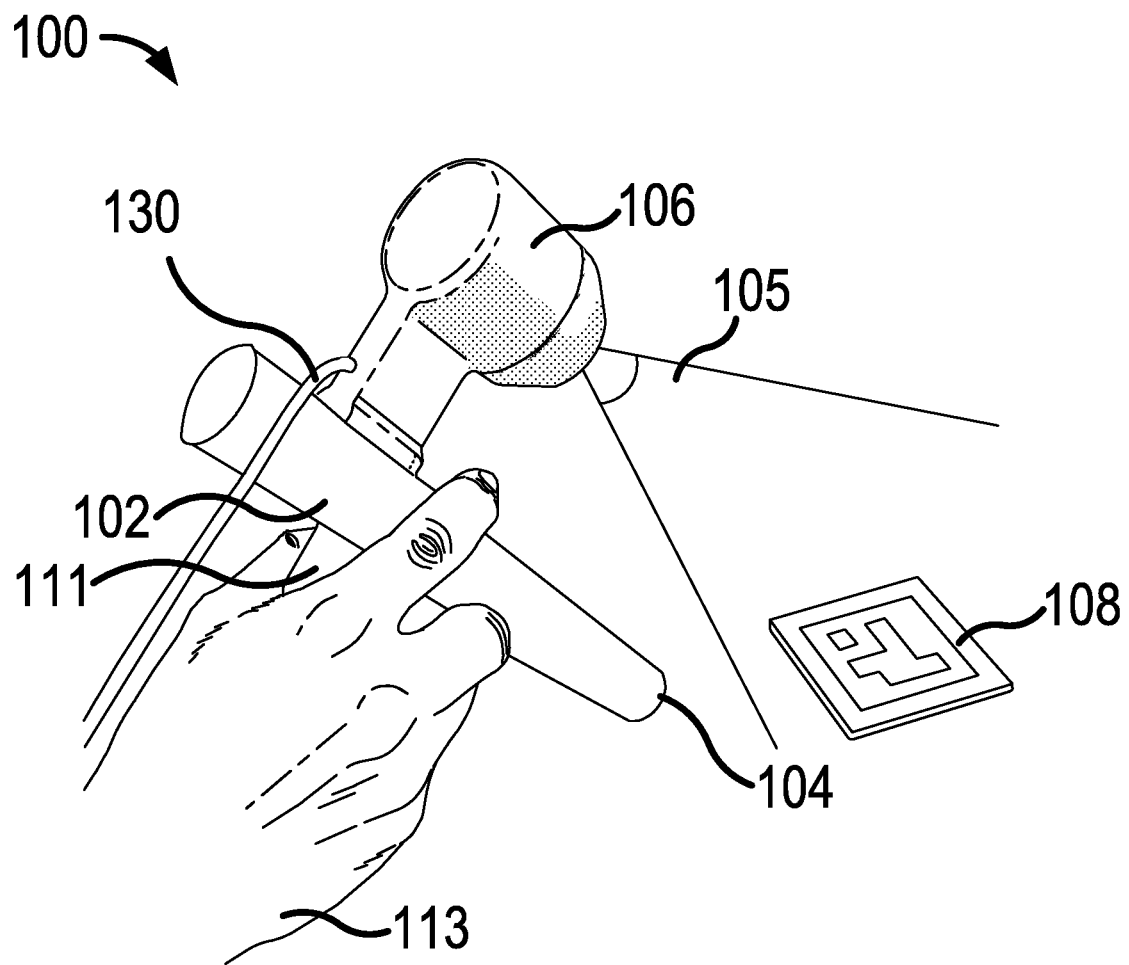
FIG. 1 illustrates a hand held medical navigation apparatus in accordance with an embodiment.

FIG. 1 illustrates a hand held medical navigation apparatus 100 that includes a housing 102, a position sensitive detector 104, a tracking camera 106, and a handle 111. The tracking camera 106 has a tracking field of view 105 and is at a predetermined proximity to the position sensitive detector 104.

The medical navigation apparatus 100 includes at least one processor (not shown) and a memory (not shown), either within the housing 102 or in an external processing unit, that is coupled with the tracking camera 106. Using instructions provided within the memory, the processor determines the spatial position and orientation of images captured by the tracking camera 106 with respect to one or more fiducial markers 108. The memory has further instructions to associate scanning data collected by the position sensitive detector 104 with the calculated spatial position and orientation of the images from the tracking camera 106 to determine a position and orientation of the scanning data using the known proximity of the tracking camera 106 and the position sensitive detector 104. In some embodiments, the images and scanning data collected can be combined to construct a (two-dimensional or three-dimensional) model to visualize the area scanned. In the course of use, the hand of the user 113 grasps the handle 111 and can scan an area of interest by moving the medical navigation apparatus 100 around an area of interest. When the memory and processor are in an external processing unit, the tracking camera 106 and the detector 104 can be connected using one or more wires 130.

Non-limiting examples of tracking cameras useful in the medical navigation devices described herein include a visible light camera, an IR (infra-red) camera, a time-of-flight camera, a structured light camera, a stereoscopic camera, another depth sensing camera, or a combination thereof.

Non-limiting examples of position sensitive detectors are known in the art and include magnetic sensors, electromagnetic sensors, radiation detectors. A person of skill in the art will recognize that the position sensitive detectors can be a gamma ray probe, an ultrasound sensor, a spectroscopic camera, a hyperspectral camera, a fluorescence imager or any other known position sensitive detectors in the art.

The relative position and orientation of the tracking camera and position sensitive detector can be adjusted based on the design needs of the user.

The fiducials 108 used during tracking can include markers with binary coding applied in the proximity of the area of interest, markings added to the body, natural marks present on a subjects body, the shape of the patient body, or any other useful reference point of known location. There may be 1, 2, 3, 4, 5, 6, 7, 8, 9, 10, or as many fiducials as necessary to accurately determine the location of any signals. Fiducials that are added to the skin may include an adhesive material that allows for secure fastening to the user. Added fiducials can be of any suitable shape including a square, a rectangle, an 'L' shape, a 'V' shape, a 'T' shape, or a 'U' shape. One fiducial can be of the desired shape, or multiple fiducials can be placed in an arrangement to form the desired shape.

The tracking camera can be used to create a 3-D model of the patient's body contour by using depth imaging data, structure from motion algorithms, or other computer vision approaches. Markings added to the skin of the patient visible to the tracking camera can improve the 3-D modeling performance, especially when using stereoscopic systems or monocular systems along structure from motion type of algorithms.

In some embodiments, an object of interest is scanned instead of a patient's body.

In some embodiments, other tracking sensors, such as IMUs (inertial measurement units) or magnetic sensors mounted onto the body of the sensing device, or other external tracking systems, can be used to augment the tracking capabilities of the tracking camera.

In some embodiments, the scan can be performed using a mechanical system in which moves the apparatus with mechanical actuators that keep a precise track of device movements. In some embodiments, these mechanical actuators can be part of a surgical robotic system, such the Da Vinci Surgical System. Other tracking modalities, such as magnetic, ultrasonic or electromagnetic trackers can be used.

Figure 2:
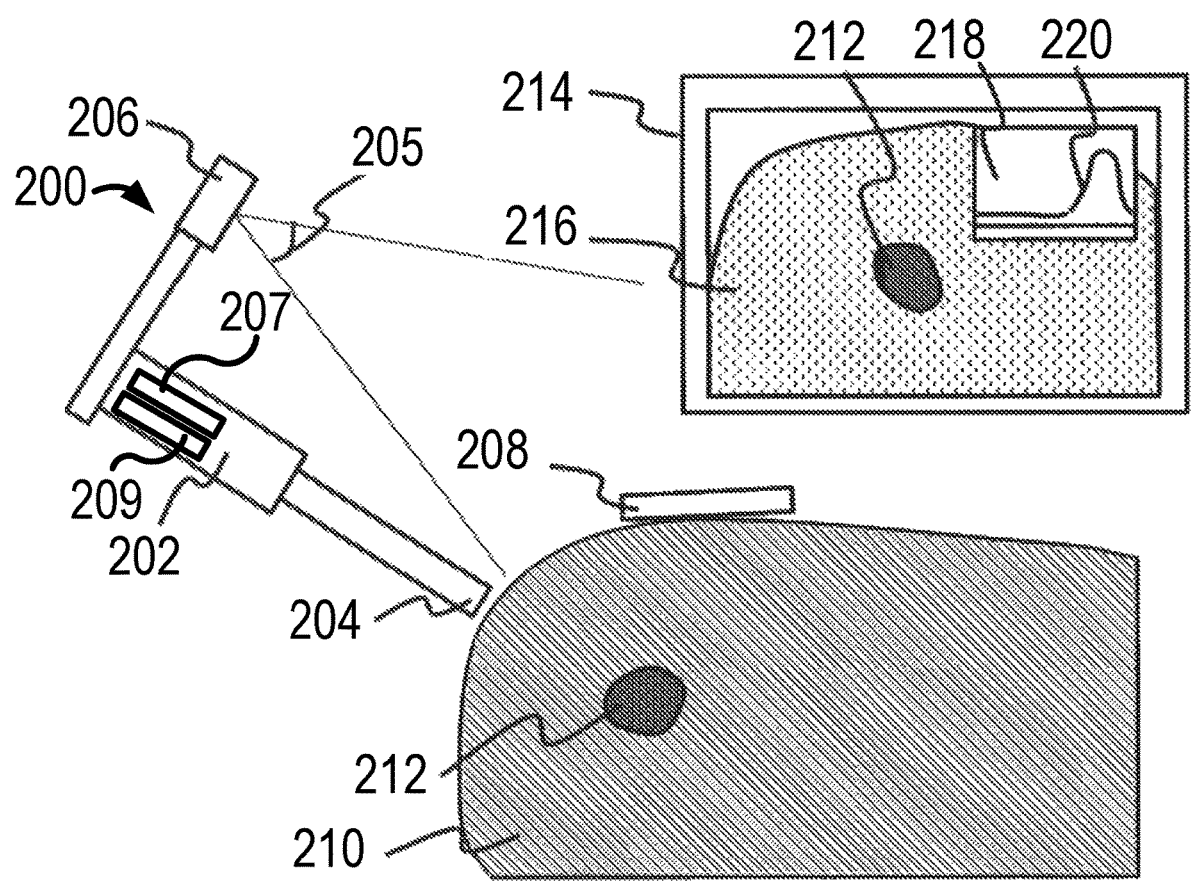
FIG. 2 illustrates the use of a medical navigation apparatus in accordance with an embodiment.

FIG. 2 illustrates the use of a medical navigation apparatus 200 that includes a housing 202, a memory 207, a processor 209, a position sensitive detector 204, and a tracking camera 206. The tracking camera 206 has a tracking field of view 205 and is at a predetermined proximity to the position sensitive detector 204. During the scan, medical navigation apparatus 200 is positioned such that the position sensitive detector 204 and the tracking camera 206 are pointed towards the subject's body 210. The position and orientation of the tracking camera 206 is determined with respect to one or more fiducials 208, and scanning data collected by the position sensitive detector 204 is associated with the calculated spatial position and orientation of the images from the tracking camera 206 to determine a position and orientation of the scanning data using instructions provided in the memory and executed by the processor, as described in FIG. 1. The images from the tracking camera 206 and scanning data from the position sensitive detector 204 are combined by the processor to form a model that is presented on a display 214 showing a graphical user interface 216 that shows the constructed model and other information collected during the scan. The graphical user interface 216 also include a window 218 that shows a graphical representation of the depth profile 220 between the signal 212 and the position sensitive detector 204 is shown. In some embodiments, the display can be any useful visualization device.

In embodiments including a graphical user interface, the graphical user interface can include one or more windows displaying other information collecting during the scan. Information that can be shown on the graphical user interface includes images from the tracking camera, scanning data displaying the relative location of any signals, and the combined images from the tracking camera and scanning data. The combined images and scanning data can be represented as an overlapped image, a two-dimensional model, or a three dimensional model.

In embodiments with more than one window in the graphical user interface, one or more of these displays can be shown. Further information displayed in the graphical user interface windows includes graphical plots reporting the measured signal intensity and distance as well as a target display reporting the location of the detected signals with respect to the alignment with the detector.

The depth profile graphical display can include a continuous plot, a histogram plot, or any other plot that graphically represents distance. In both the continuous and histogram plot, a y-axis represents the amplitude or amount of signal detected, while an x-axis represents the distance. In some embodiments, the axes can be reversed.

Generally, the field of view of the tracking camera is large enough to cover the area of interest from a range of positions and orientations that befit the application. The field of view can be altered to fit the particular needs of the desired application.

The housing of the medical navigation apparatuses described herein can be made out of any suitable material. That material can include metal, a rigid polymer such as a thermoset plastic. Examples of such thermoset plastics include polyurethanes, polyesters, epoxy resins, phenolic resins, or copolymers of such plastics.

Although FIGS. 1-2 show the camera out of plane with the detector, the position of the camera can be moved to anywhere to fit the needs of the desired application. Furthermore, the orientation of the camera with respect to its field of view can also be manipulated to fit the needs of the desired application.

Figure 3:
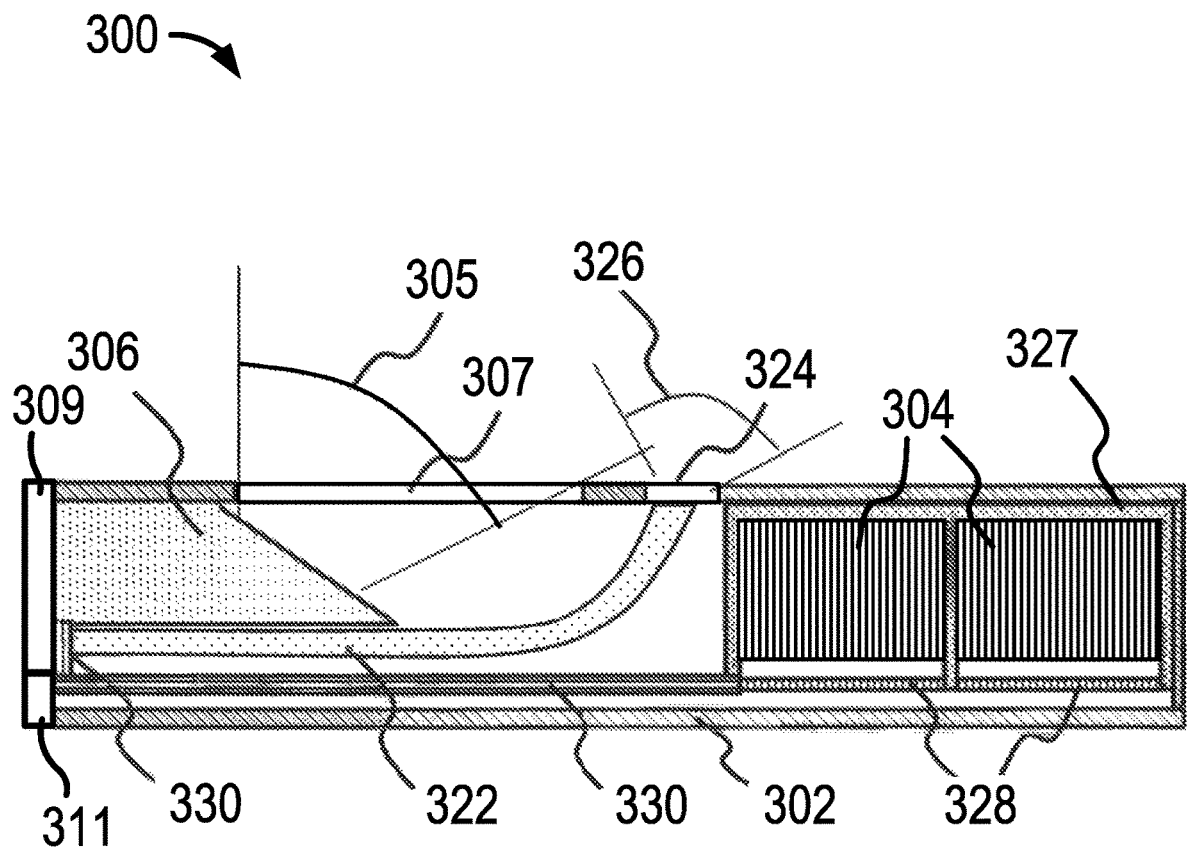
FIG. 3 illustrates a cross sectional view of a medical navigation apparatus in accordance with an embodiment.

FIG. 3 illustrates a cross sectional view of a medical navigation apparatus in accordance with an embodiment. Medical navigation apparatus 300 contains an elongated housing assembly 302, gamma ray probes 304 disposed at a distal end of the housing assembly, and a tracking camera 306 having a tracking field of view 305 that is lateral to the longitudinal axis of the housing assembly, the tracking camera 306 having a known proximity to the position sensitive detectors 304. The housing assembly 302 includes a transparent optical window 307 which provides the tracking camera 306 a tracking field of view 305. The housing assembly also includes an optical fiber 322 and a transparent illumination window 324 providing an illumination field of view 326 that overlaps with the tracking field of view. The position sensitive detectors 304 are within a matrix 327 that provides electrical isolation and protection from mechanical shock. In some embodiments the matrix is present. In some embodiments the matrix is not present. The detectors 304 are operably connected to read out boards 328 that can provide electrical power to the detectors. The boards can also host signal processing circuitry, such as Application Specific Integrated Circuits (ASICs) or other processors. Other arrangements of the read-out boards and detectors are possible. For example the boards and the attached detectors can be placed perpendicular on the symmetry axis of the housing. Wires 330 also connect gamma ray probes 304 and tracking camera 306 to a memory 311 operatively coupled with a processor 309.

In some embodiments, this medical navigation apparatus is suitable for laparoscopic or other intra-cavity examinations or surgeries. The laparoscopic device may be any useful shape. In some embodiments, intra-cavity medical navigation apparatus is cylindrical. In some embodiments, the intra-cavity medical navigation apparatus is rectangular. When used in laparoscopic surgeries or other intra-cavity procedures, the cylindrical radius is about 35 mm, preferably 30 mm, more preferably less than 30 mm.

In some embodiments, the position sensitive detectors 304, are a single detector. In some embodiments, there are two, three, four, or more detectors.

The position sensitive detectors can be any useful detectors known in the art. Non-limiting examples of detectors include a gamma ray probe, an ultrasound sensor, a spectroscopic camera, a hyperspectral camera, a fluorescence imager. Examples of materials that are used for gamma ray probes include semiconductor detectors such as silicon (Si) detectors, silicon lithium (Si(Li)) detectors, germanium (Ge) detectors, germanium lithium (GeLi) detectors, cadmium zinc tellurium (CdZnTe) detectors, cadmium tellurium (CdTe) detectors, mercuric iodide (HgI2), lead iodide (PbI2), a position sensitive scintillator crystal, multiple position sensitive scintillator crystals, segmented Si detectors, pixelated electrodes, parallel strip electrodes, co-planar strip electrodes, depleted CCD sensors, depleted CMOS sensors, or any other sensor known in the art. Examples of ultrasound transducer include piezoelectric crystal, capacitive micro-machined ultrasonic transducers (cMUTs), or any other type of ultrasonic transducer. In embodiments comprising more than one detector, each detector is independently selected. These sensors are preferably of sizes around 1 cm×1 cm×1 cm, but larger or smaller detectors can be used.

In some embodiments the transparent optical window 307 and the transparent illumination window 324 are a single window.

In some embodiments an illumination source is provided that is not an optical fiber. A person of skill in the art will recognize that any illumination source can be included. In fact, the illumination source can include a constant light, spatially patterned light, spectrally coded light, time coded light, uniform light, or combinations thereof.

In some embodiments the position sensitive detector is a collimator-less gamma ray probe with a 4 pi field of view. The memory of this radiation position sensitive apparatus includes instructions for execution by a processor to convert scanning data collected by the gamma ray probe into a reconstructed diagram identifying the location of a radiation source relative to a fiducial. The reconstructed diagram can be produced from the scanning data using Compton imaging, self-collimation effects, proximity imaging or any known means in the art. The reconstructed diagram can be shown in a display window in embodiments where a display and a graphical user interface are included.

Image reconstruction of tracer distribution can be done by using Compton imaging, self-collimation effects and/or proximity imaging. If the position sensitive detector can provide electron track information, the shape of an least one electron track per detected event can be used to reconstruct the direction and energy of the incident radiation. Electron tracks can be used to image gamma rays as well as beta rays emitted in close proximity to the sensor. This collimator-less camera system can be used as is, without any tracking capabilities, or tracking methods can be used to locate the position and orientation of the imaging sensor with respect to the body of the patient. This collimator-less imaging sensor system can be used from the outside of the body of the patient, or it can be body-insertable, such as laparoscopic. All the embodiments described above for sensor systems can apply to this collimator-less imaging sensor system. When resolving the shape of the electron tracks is not possible, a computer operationally coupled to the sensor can calculate a scattering angle around a scattering direction of a gamma ray interacting at least two times in the sensor system by resolving the kinematics of the gamma ray interactions within the sensor system. The kinematics is resolved by conserving the energy and momentum for Compton interactions taking place within the sensor system.

The determined scattering angle around a scattering direction creates a cone on the surface of which the gamma-ray must have originated from. By accumulating several scan, multiple cones can be created. A statistical image reconstruction algorithm known in the field can be used to reconstruct the map of sources from the set of cones. For a more accurate image reconstruction, other factors can be accounted for, such as attenuation in the tissue, as well as self-attenuation within the sensor. For the case when the sensor is being tracked, the computer can associate gamma ray interaction data from the sensor with the calculated spatial position and orientation of the sensor with respect to the adjacent object or examined object to create registered scans. The image reconstruction will then use cones that are spatially registered in a 3-D space, allowing for the reconstruction of a 3-D map of sources.

In some embodiments, the position sensitive detector and the tracking camera are operably coupled to the memory and at least one processor without wires. In embodiments where no wires are used, the detector and tracking camera can be operably coupled using any known means in the art including a BLUETOOTH® device or a wireless router.

The transparent optical window can be made of any suitable material. Such materials include, but are not limited to glass, polycarbonate, lexan, ceramic, and other rigid clear polymers. Similarly, the transparent illumination window can be any of these materials as well. In some embodiments, the transparent illumination window is the same material as the transparent optical window. In some embodiments, the transparent illumination window is a different material then the transparent optical window.

Figure 4A:
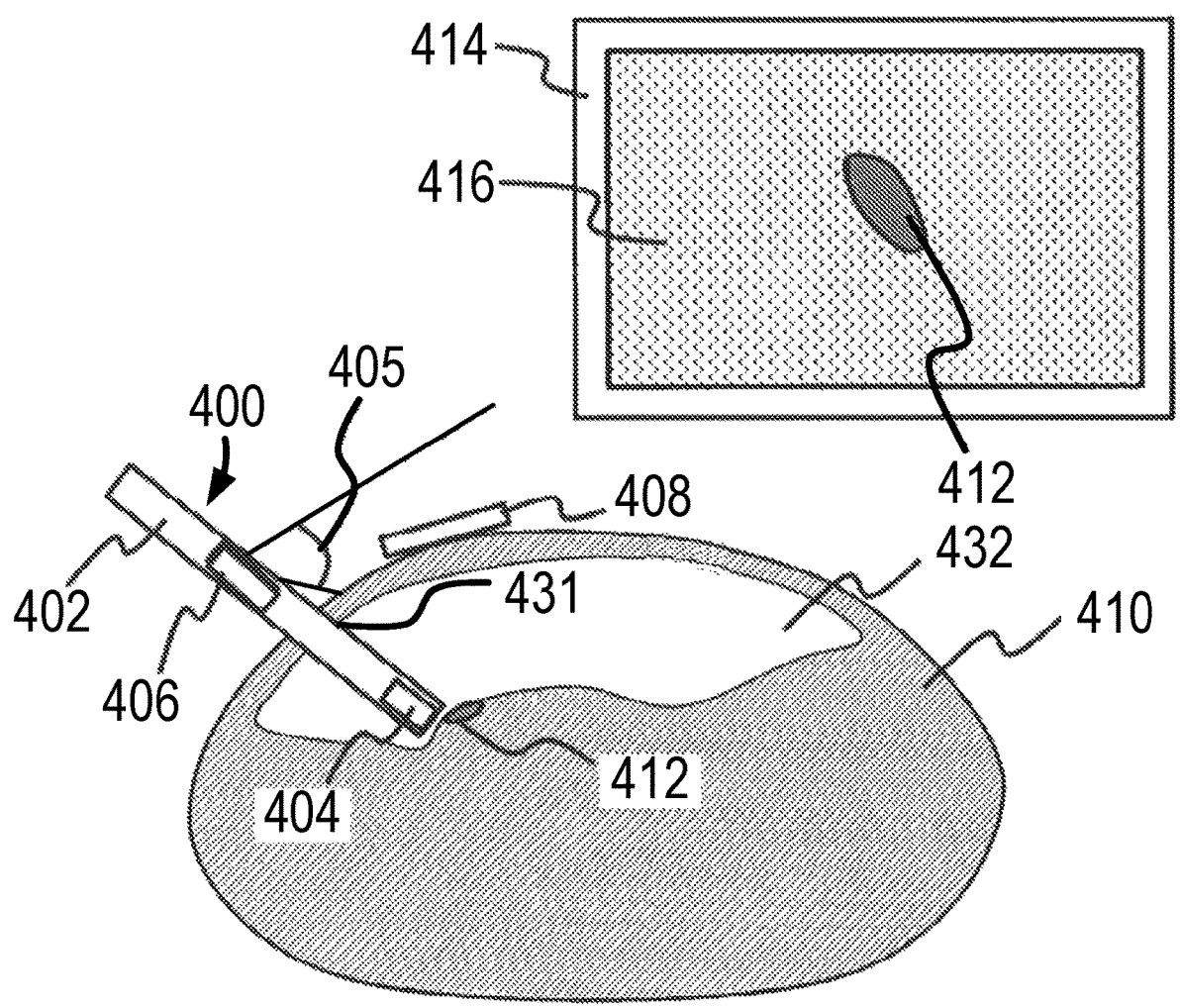
FIG. 4A illustrates use of a medical navigation apparatus in accordance with an embodiment.
Figure 4B:
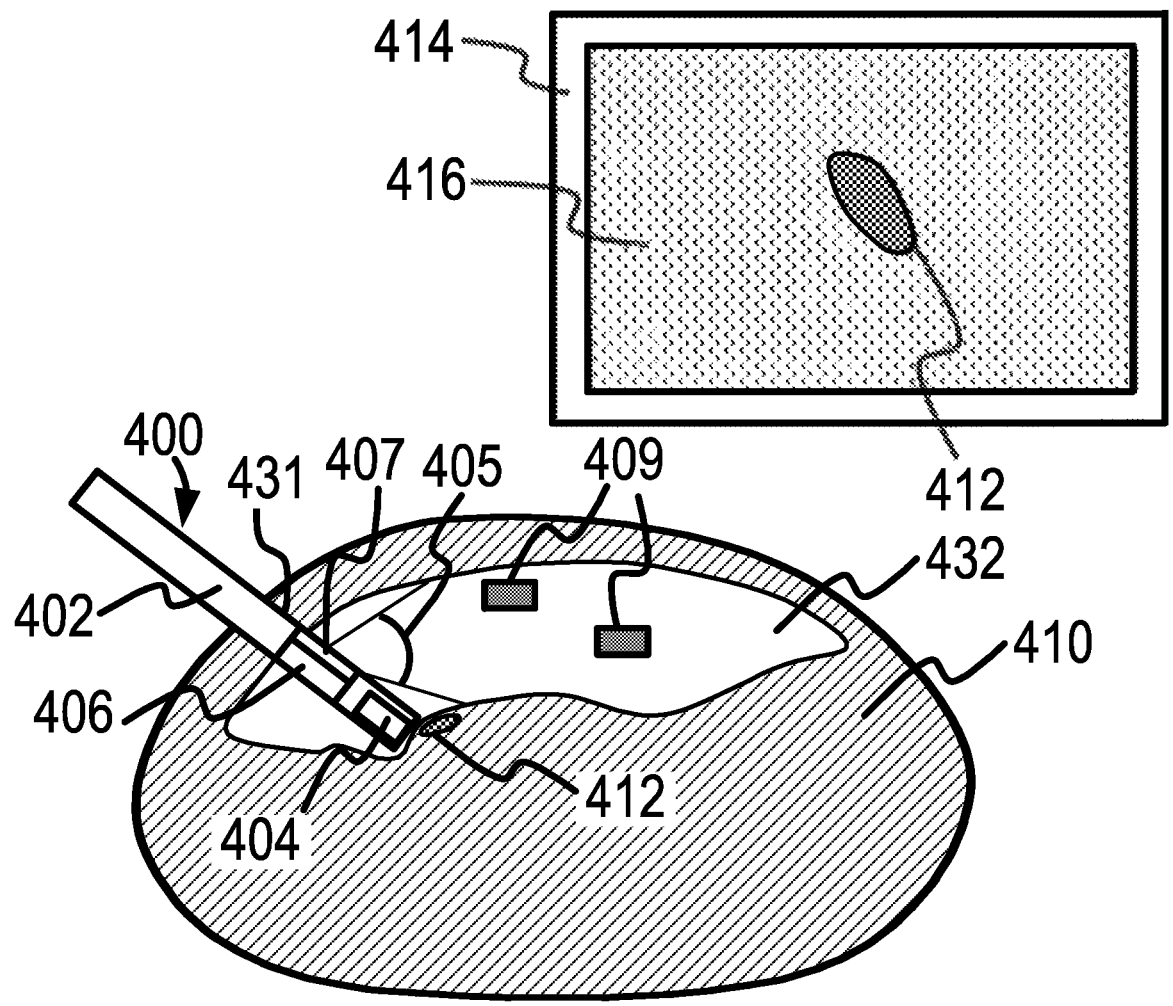
FIG. 4B illustrates use of a medical navigation apparatus in accordance with an embodiment.

FIGS. 4A and 4B illustrate the use of a medical navigation apparatus in laparoscopic surgery. The body of a patient 410 includes a small cavity 432 that creates an open space to perform the surgery. The apparatus 400 contains an elongated housing unit 402 that is inserted through an incision 431 into the cavity 432. The medical navigation apparatus 400 includes a position sensitive detector 404 and a tracking camera 406 having a tracking field of view 405 that is lateral to the longitudinal axis of the housing assembly, the tracking camera being a known proximity to the position sensitive detector 404. The position sensitive sensor can detect a signal 412 emanating from the scanning area.

In FIG. 4A the tracking camera 406 is located outside of the laparoscopic cavity 432 and position and orientation information is collected with respect to a fiducial 408 that is located outside the body.

In FIG. 4B the tracking camera 406 is located inside of the laparoscopic cavity 432, and position and orientation information is collected with respect to one or more fiducials 409 within the body. The medical navigation apparatus 402 in FIG. 4B further comprises a device 407 configured to supply a stream of fluid in order to keep the transparent optical window and the tracking field of view 405 clear.

Scanning data collected by the position sensitive detector 404 in both FIGS. 4A and 4B is associated with the images from the tracking camera 406 to determine a position and orientation of the scanning data using the known proximity of the tracking camera 406 and the position sensitive detector 404. The images from the tracking camera 406 and scanning data from the position sensitive detector 404 are combined by the processor to form an model that is presented on a display 414 showing a graphical user interface 416 that shows the constructed model.

The fluid used to keep the tracking field of view of the tracking camera clear can be any useful liquid or air. Such useful liquids include, but are not limited to, water or saline.

In embodiments including a transparent optical window, the transparent illumination window can include a device configured to supply a stream of fluid to keep the transparent illumination window clear. The fluid can be any useful liquid or air. Such liquids include, but are not limited to water or saline.

In some embodiments the fiducials inside the body are tissues of known location. In some embodiments, the fiducials inside the body are markers placed in known locations of the investigated area by medical personal performing the procedure. In embodiments where fiducials are marked placed in known locations of the investigated area, the fiducials can include marks with a binary coding.

Although laparoscopic surgery is an exemplary embodiment described herein, a person of skill in the art will recognized that the apparatuses described herein can be used in various types of surgery and can be used externally or internally. By using an internal camera, internal values such as organs can be mapped.

Although FIGS. 1-4 show the detector at the tip of the medical navigation apparatus, the position of the detector can vary depending on the desired function of the apparatus. The detector can be located anywhere within the housing.

Figure 5A:
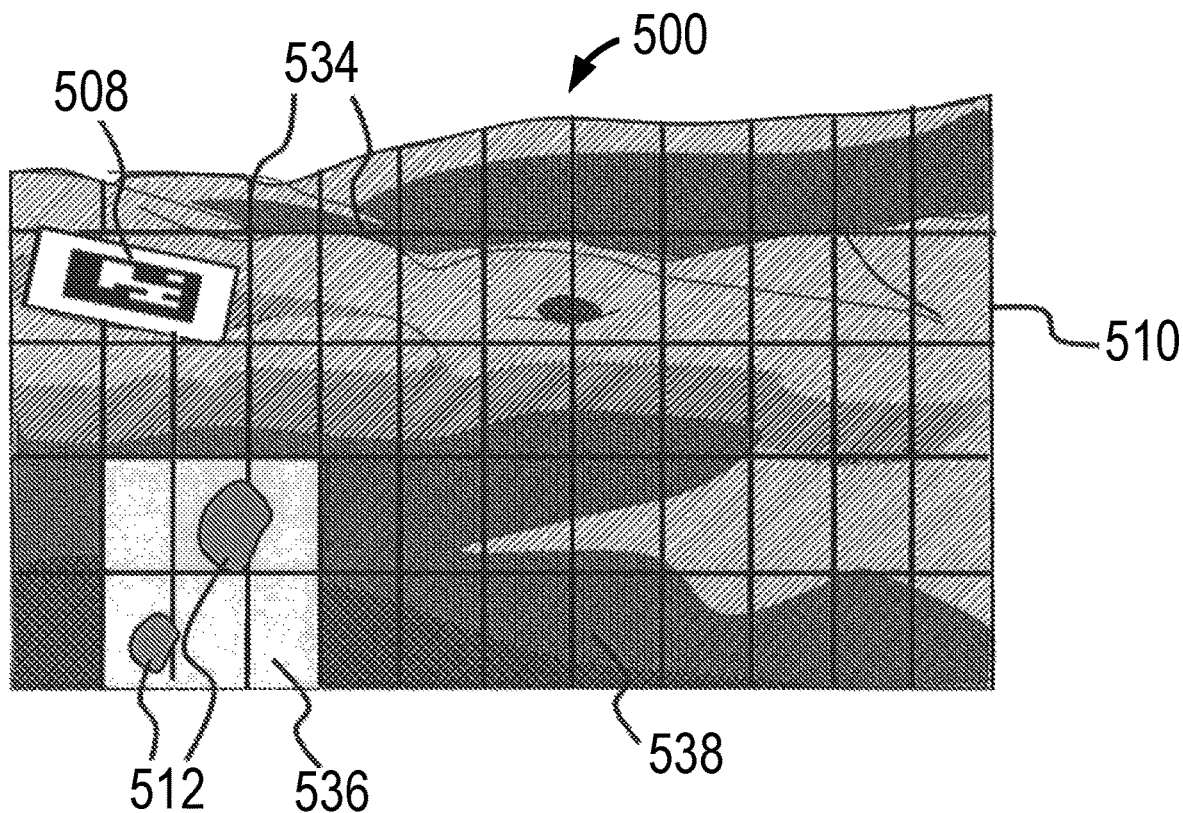
FIG. 5A illustrates a model showing combined images from the tracking camera and scanning data from the detector in accordance with an embodiment.

FIG. 5A illustrates a model showing combined images from the tracking camera and scanning data from the detector in accordance with a scanning completeness embodiment of the invention. In accordance with this embodiment, a display can show instantaneous renderings of a model produced from the images collected by a tracking camera and scanning data collected by the position sensitive detector using any of the devices described herein. The scanning sufficiency model 500 shows the body 510 of the subject divided into gridlines 534. Also shown is a fiducial 508 that has been applied to the body of the subject to perform the scan. The gridlines 534 separate the body 510 into individual volumetric units (voxels).

A "voxel" includes an individual imaging element of volume that represents separating adjacent volumetric space, or as otherwise known in the art. Voxels can be displayed in two dimensions or three dimensions. Voxels can be broken into any useful shape including rectangles, squares, triangles, prisms, cylinders, cones, or cubes. In some embodiments the gridlines may be displayed on the display. In some embodiments, the gridlines are not visible on the display.

A sufficiently scanned voxel 536 appears translucent or "see through," while an insufficiently scanned voxel 538 appears opaque. Any signals 512 detected in the sufficiently scanned voxels 536 are clearly visible in the model. As the scanning completeness increases in each voxel, the opaqueness of the voxel erodes.

Figure 5B:
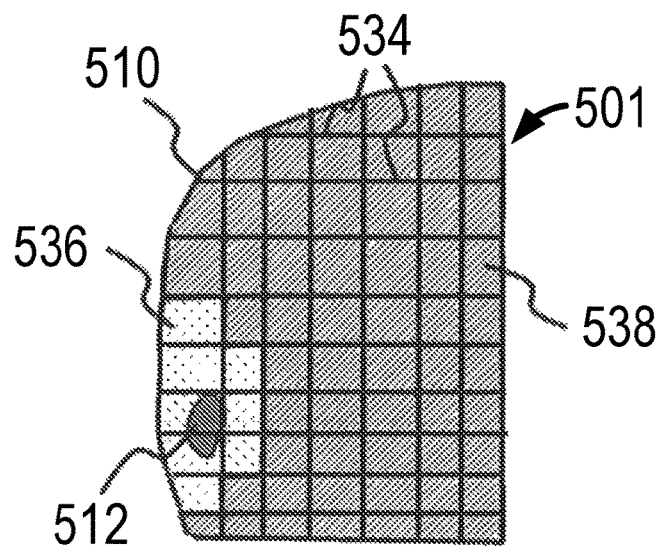
FIG. 5B illustrates a cross section of a model showing combined images from the tracking camera and scanning data from the detector in accordance with an embodiment.

FIG. 5B illustrates a cross section of a model showing combined images from the tracking camera and scanning data from the detector in accordance with a scanning completeness embodiment of the invention. The scanning completeness model cross section 501 of body 510 is broken up by gridlines 534 into individual volumetric units (voxels). Insufficiently scanned voxels 538 appear opaque, whereas sufficiently scanned voxels 536 appear translucent or "see through." Any signals 512 detected in the sufficiently scanned voxels 536 are clearly visible in the model.

Completeness of scanning in the individual voxels can be determined, for example by assigning each voxel a scanning completeness value (SCV). Before the scanning start, the SCV may be set to zero. As each voxel is being scanned, its SCV value will grow indicating if the scanning of that particular volumetric unit is sufficient. An exemplary method of calculating scanning completeness value is by equating the SCV to the voxel effective sensitivity. The voxel effective sensitivity may be calculated by summing the probability by which a signal emitted or reflected inside that volumetric unit is detected by the scanning sensor at each moment of time, over the scanning period. It is understood that other statistical calculations of the SCV can be performed. For example, a number that represents the minimum quantity of signal that can be present in each volumetric unit, may be used to indicate scanning coverage. This value may be named the Minimum Detectable Quantity (MDQ).

In some embodiments, the scanning completeness model is a two-dimensional model of images captured by the tracking camera. In some embodiments the scanning completeness model is a three-dimensional model of images captured by the tracking camera. The three-dimensional model can be shown as a 3D mesh. More extensive or complex 3-D renderings can be also shown. In some embodiments, the scanning completeness model is an overlapped view of the scanning data and the images captured by the tracking camera.

When a particular voxel has been sufficiently scanned, the user will receive a notification. This notification can be communicated to the user in a variety of different means.

For example, the notification can be voxels shown on a display screen changing from opaque to "see through" voxels on a display screen changing color. Additionally the notification can include the apparatus providing an audible sound to a user when a particular area has been sufficiently scanned or a light indication on the apparatus when a particular area has been sufficiently scanned.

Often, when a human operator performs a scanning procedure using a hand-held sensing or imaging device, coverage of the scanning area may be incomplete or uneven, leading to incomplete or biased results. Therefore, it may be very important to provide tools to guide the operator during the scanning process for a better quality, and more complete scan. For example, when using a gamma sensor such as a gamma probe, a gamma camera, other ionizing radiation sensor or other statistics sensitive sensors to image tracers or markers, the magnitude of signal taken from a certain area is proportional with the time the sensor is adjacent to that particular area, and is sensitive to that particular area. A larger overall signal increases the data statistics and decreases the data noise that is fed into the image reconstruction algorithm, having the end result of providing images with better resolution, higher contrast and lower noise. A subject of this invention is to describe a scanning sufficiency apparatus and method. When such a statistics sensitive sensor is moved through an environment, a tracking system may be used to track continuously the position and orientation of the sensor with respect to objects in the adjacent environment. A computer operationally coupled to the sensor and the tracking system can keep track of the whole scanning history, associating scanning data with sensor position and orientation. Tracking systems used for this purpose can use mechanical displacement means, magnetic signals or waves, electromagnetic signals or waves, optical means, can use beacons or be self-sufficient. These spatially registered scans can be analyzed by the computer to create a 3-D distribution of sources creating the signatures measured by the sensor. Iterative or analytical image reconstruction algorithms known in the field can be used to create such 3-D maps. These 3-D maps will cover a volumetric space called image space. This image space may be separated into small volumetric units, such as voxels, and to each voxel, a scanning completeness value (SCV) can be assigned. The scanning tracking history may be used to calculate SCV and may inform the user about the partial volumes that have been scanned enough and the partial volumes that have not been scanned enough for a pre-defined scanning objective. SCV can be calculated in multiple ways. In one embodiment, the calculation of the SCV takes into account the summation of the probabilities that the signal emitted by a radioactive source inside the imaging element is detected by the sensor at each moment of time over the scanning period. In another embodiment the SCV can represent a value that accounts for the minimum quantity of tracer or marker that can be present in each volumetric element given the scanning history and the reconstructed image. In another embodiment the calculation of the SCV takes into account the coverage of directions from which the sensor observed the imaging element over the scan period. The user could be given indications about locations and orientations where more scans should be taken for a more complete data set. A more complete data set can allow formation of images that have better resolution, better contrast, lower noise, provide detection of lower detectable quantities of sources, or a combination thereof. A visualization device operationally coupled to the computer can be used to show an instantaneous image representing a rendering of the SCV map. When a camera co-registered with the sensor is used, the visualization device could show the rendering of the SCV augmented onto an essentially life image provided by the camera. Likewise, other renderings can be combined with the rendering of the SCV, such as a rendering of the 3-D map of sources, life images from cameras or other co-registered imagery or renderings.

A tag may be used to support the determination of the camera position and orientation with respect to the body of the patient. It is understood that more than one tag may be used, or no tag may be necessary. In some embodiments the computer attached operationally to the tracking camera can determine the 3-D model of the patient body contour. When using at least an RGB or IR camera as tracking camera, markings visible to the tracking camera can be drawn on the skin of the patient, or stickers with markings can be placed on the skin to augment existing image features that may exist on the skin of the patient. Using the images taken by the tracking camera, computer vision specific feature detectors, feature trackers and meshing techniques can be used to build a 3-D model of the patient body contour. Having available the 3-D mesh of the patient body, voxel occupancy techniques can be implemented in the computer to determine what part of the space is occupied by the body of the patient. That occupied space may be separated in small volumetric units, such as voxels, and to each voxel, a scanning completeness value (SCV) can be assigned. However, if the contour of the patient's body may not be determined, the whole adjacent space may be separated in such small volumetric elements for the calculation of the SCV. Before the scanning start, the SCV may, for example, be set to zero. As a specific voxel from the group is being scanned, its SCV value will grow indicating if the scanning of that particular pixel is sufficient. An example of calculating SCV is by equating it to the voxel effective sensitivity. The voxel effective sensitivity may be calculated by summing the probability by which a signal emitted or reflected by the tracers or markers inside that pixel is detected by the scanning sensor at each moment of time, over the scanning period. It is understood that other statistical calculations of the SCV can be done. For example, a number that represents the minimum quantity of tracer or marker that can be present in each pixel, may be used to indicate scanning coverage. This value may be named the Minimum Detectable Quantity (MDQ).

In order to intuitively present to the operator the distribution of voxels that have been sufficiently scanned, or insufficiently, over the scanning period, a rendering of the image representing one or more versions of SCV can be performed and displayed. In some embodiments, the rendering of the SCV map can be overlapped onto the visual streaming image taken by the tracking camera or other camera whose position and orientation is known in respect to the patient. In such embodiments, the pixel intensity from a selected area in the video stream can be modified to indicate skin transparency. The rendering of the SCV map may, for example, be performed so that, voxels with incomplete scanning show transparent, and voxels with sufficient scanning show more opaque and/or with a higher intensity color. Various volumetric rendering or maximum intensity projection methods can be used for the visualization of the SCV map. Alternatively, the rendering of the SCV map may be performed so that, voxels with incomplete scanning show opaque, and voxels with sufficient scanning show more transparent. An advantage of this second visualization approach is that the voxels that become transparent can leave a clear line of sight to visualize a rendering of the 3-D sensor created map that may form in the areas being scanned. The resulting visual effect will be that, as the sensor scans a certain volume, that volume will become transparent (or eroded), leaving behind volumetrically rendered colored voxels corresponding the highest intensities in the sensor produced images.

The change in opacity to full transparency may appear gradual, or in discrete steps. Using discrete steps may help give the operator a better impression of volume, especially when 3-D displays are not used for visualization. One example in which discrete steps can be used is when only 2 transparency values are used: full transparency and full opacity. For example, the transition between the two states may be set at a point where the calculated MDQ for a specific volumetric element reaches a preset value. For example, when the volumetric element's MDQ is above that limit, full opacity can be associated with that volumetric element, when the MDQ is below that limit, full transparency can be associated with that volumetric element. The value of the preset MDQ may vary and may be determined by the particular scope of the measurement.

In embodiments in which the 3-D modeling of the patient body contour is not used, no pre-computed pixel occupancy may be calculated, and the whole space around the sensing device is analyzed for scanning completeness, being similarly visualized.

Alternatively, or additionally to navigating the 3-D sensor produced image by using the streaming video from the tracking camera mounted on the sensing device, itself, the streaming video from another tracking camera mounted on another medical instrument or tool can be used. Examples of such tools are: a surgical marking pen, a laser pointer, a surgical instrument, or a basic pen-like object.

Figure 6:
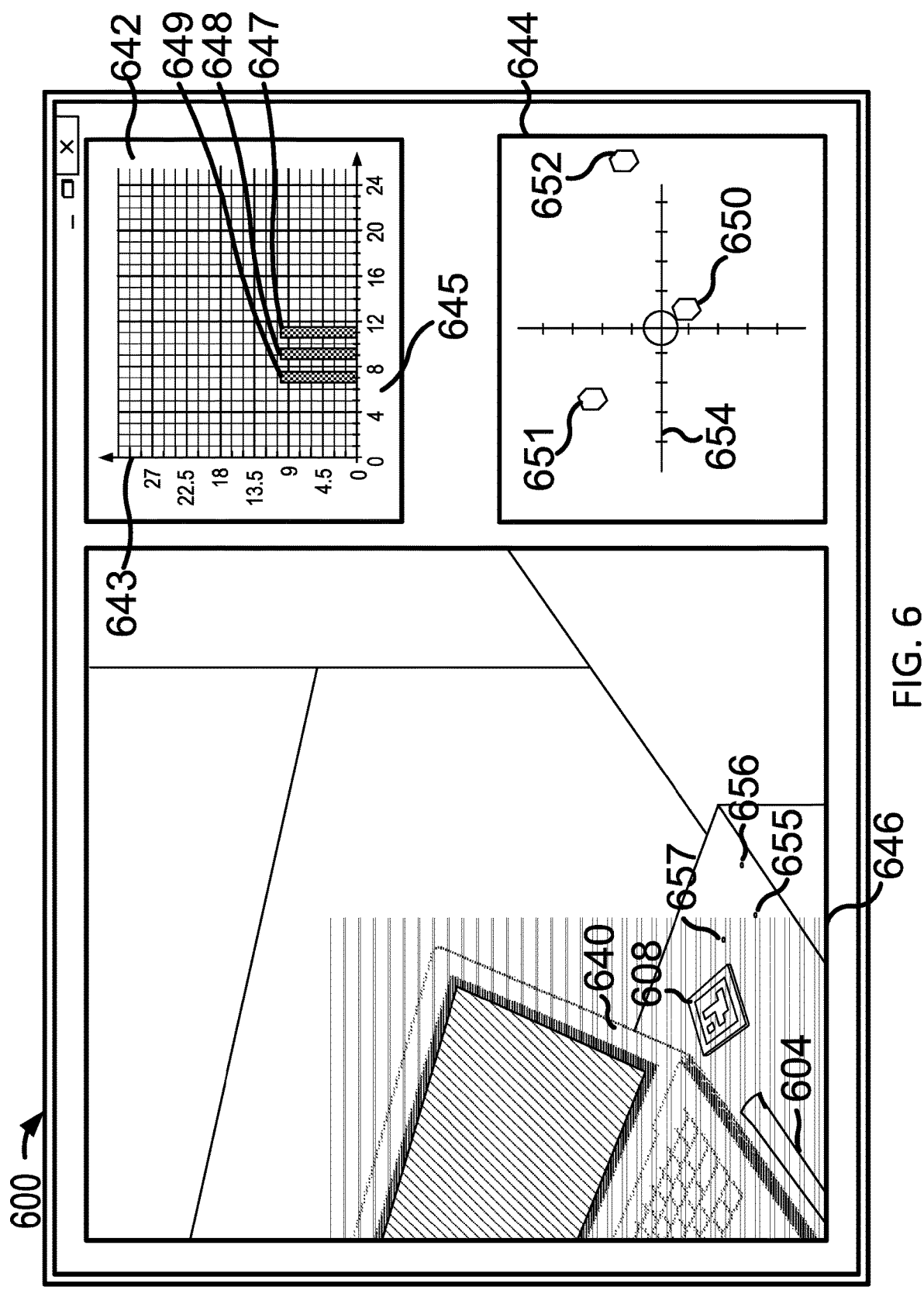
FIG. 6 illustrates a view of a graphical user interface in accordance with an embodiment.

FIG. 6 illustrates a view of a graphical user interface in accordance with an embodiment. The graphical user interface 600 includes three windows 642, 644, and 646, each of which present different information to the user. Projection window 646 is showing an overlapped view of instantaneous images from the tracking camera and instantaneous scanning data from the detector 604. In the projection window 646, object 640 and fiducial 608 are shown.

The contains three markings 655, 656, 657 shown in window 646 correspond to the location of signals detected by the detector 604. Graphical window 642 shows a histogram plot where on the y-axis 643 the intensity of the detected signal, in this case gamma radiation, is shown and on the x-axis 645 the distance between the source of the signal and the detector is shown. The distance and amplitude represented by column 649 corresponds to marking 655, column 648 corresponds to marking 656, and column 647 corresponds to marking 657. Target window 644 shows an x, y scatter 654 of each detected signal with respect to the alignment of each signal with the detector. When a signal is located at the x-y intersect, the detector is completely aligned with that given signal. In the target window 644, detected signal 650 corresponds to marking 655, detected signal 651 corresponds to marking 657, and detected signal 652 corresponds to marking 656. This view can be helpful when the operator of the device is trying to position the detector directly in line with a particular signal.

The graphical user interface can include any number of windows presenting data from the scan. The windows can include images from the tracking camera, scanning data from the detector, combined images from the tracking camera and scanning data from the detector, a model of the combined images and scanning data, a cross section of the model, a view of the model from a particular angle, graphical representation of the depth of any signals detector, or a target view showing the position of signals detected with respect to their alignment with the detector.

Figure 7:
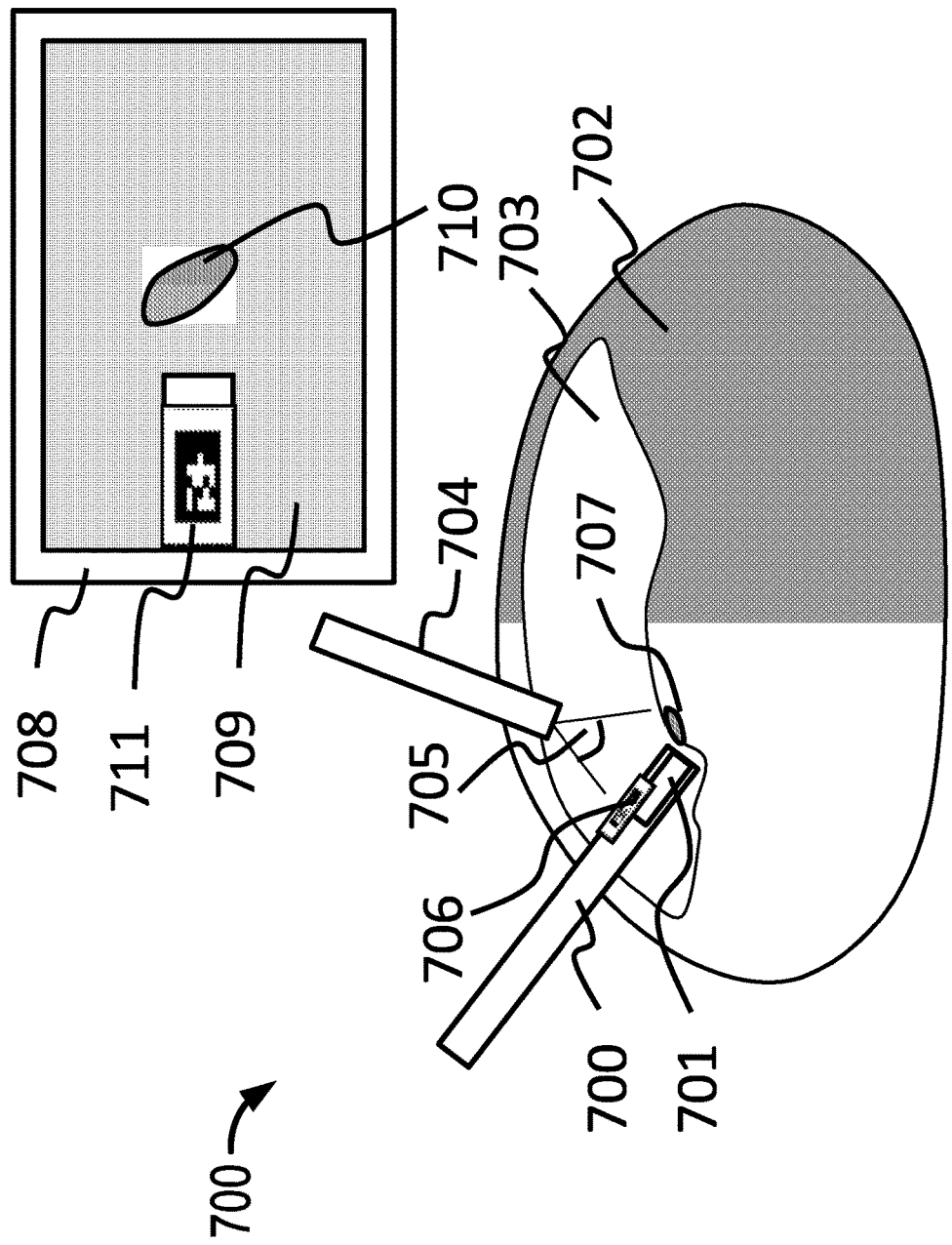
FIG. 7 illustrates the use of a medical scanning apparatus and an external tracking camera in accordance with an embodiment.

FIG. 7 shows an embodiment of the invention in which a body-insertable telescopic optical system is used as a tracking camera by positioning it to observe the sensor system. In this example, a medical sensing instrument 700 is body-insertable, being used in a laparoscopic surgery. The instrument 700 has a sensor 701 towards its distal end, with its purpose being to detect specific targets within a patient 702. In this particular example, the surgery is laparoscopic, hence a cavity 703 is formed inside the patient by inserting gas, such as $CO_2$. The sensor 701 can be any of the sensors described herein, or any other sensor. Another body-insertable medical instrument 704 can comprise an optical system that can be used as a tracking camera. The field of view of such tracking camera is represented by 705, and is oriented by the user so that it covers the general area where the sensing device 700 operates inside the cavity 703. The tracking camera can be used to observe specific features of the sensing device 700 housing in order to position it in respect to the tracking camera. The tracking camera can also be used to observe the organs and tissues exposed inside the cavity 703. Consequently, the position and orientation of the sensing system 700 with respect to the patient's organs and tissues can be determined. In some embodiments a laparoscopic optical system (telescope) can be used as medical instrument 704 housing the tracking camera system. In some embodiments, a specialized laparoscopic tracking camera system (telescope) can be used. A specialized tracking camera system can comprise a depth imaging sensor, such as time of flight, structured light, monocular or stereoscopic system. A computer operationally connected to the tracking camera can be used to build the 3-D model of the organs, and to deliver the position and orientation of sensor 701 with respect to the 3-D model.

In order to improve tracking performance, specific fiducial features, such as tags 706, can be positioned on the body of the sensing system 700. A target of interest inside the body of the patient is represented by 707. For example, this can be cancerous tissue not yet excised, a lymph node of interest, or another concentration of markers or tracers. The presence and spatial distribution of this target with respect to the patient's organs can be determined by performing an analysis on the data provided by sensor 701. This analysis can be performed on a computer operationally connected to both the sensor 701, and to the tracking camera inside instrument 704.

The image presented to the user on a visualization device is represented by the insert 708. This image can comprise the video stream taken by the optical system within the instrument 704. The image 709 taken by the optical system can be fused with a rendering 710 of the image of the target 707 as reconstructed from the sensing data provided by sensor 701. The image 711 of the sensing system 700 with a tag 706 placed on it can also appear in the streaming video image.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A radiation position sensitive apparatus, comprising:
a housing assembly having a longitudinal axis;
a gamma ray probe at least partially enclosed within the housing assembly;
a tracking camera at least partially enclosed within the housing assembly, the tracking camera having a tracking field of view, the tracking camera disposed at a predetermined proximity to the gamma ray probe;
at least one processor and a memory operatively coupled with the tracking camera, the memory having instructions for execution by the at least one processor for:
calculating a spatial position and orientation of images taken by the tracking camera with respect to an object; and
associating scanning data from the gamma ray probe with the calculated spatial position and orientation of the images to determine a position and orientation of the scanning data using the known proximity of the gamma ray probe to the tracking camera.

2. The apparatus of claim 1, wherein the memory has instructions for execution by the at least one processor configured to convert the scanning data to a reconstructed diagram identifying a relative location of a radiation source to the object.

3. The apparatus of claim 2, wherein the reconstructed diagram is produced using Compton imaging, self-collimation effects, or proximity imaging.

4. The apparatus of claim 2, wherein the memory has instructions for execution by the at least one processor configured to combine the images and the reconstructed diagram to produce a three-dimensional (3-D) model of a subject's tissue.

5. The apparatus of claim 4, further comprising:
a display screen operably linked to the at least one processor and configured to show instantaneous renderings of the 3-D model.

6. The apparatus of claim 2, further comprising:
a display screen operably linked to the at least one processor and configured to show instantaneous renderings of the reconstructed diagram.

7. The apparatus of claim 1, wherein the object comprises a fiducial.

8. The apparatus of claim 1, further comprising:
a transparent optical window along a side of the housing assembly through which the tracking camera is configured to see the tracking field of view.

9. The apparatus of claim 8, further comprising:
a device configured for supplying a stream of fluid in order to keep the transparent optical window clear.

10. The apparatus of claim 9, wherein the stream of fluid comprises air or liquid.

11. The apparatus of claim 8, further comprising:
an illumination source with an illumination field of view that overlaps the tracking field of view.

12. The apparatus of claim 11, wherein the illumination source includes an optical fiber.

13. The apparatus of claim 11, further comprising:
a transparent illumination window wherein the illumination source illuminates the tracking field of view through the transparent illumination window.

14. The apparatus of claim 11, wherein the illumination source is selected from the group consisting of spatially patterned light, spectrally coded light, time coded light, uniform light, and combinations thereof.

15. The apparatus of claim 13, further comprising:
a device configured for supplying a stream of fluid to keep the transparent illumination window clear.

16. The apparatus of claim 15, wherein the stream of fluid comprises air or liquid.

17. The apparatus of claim 1, wherein the gamma ray probe comprises an enclosed matrix surrounding a sensor.

18. The apparatus of claim 17, wherein a material of the sensor is selected from the group consisting of a cadmium zinc tellurium (CdZnTe) detector, a position sensitive scintillator, a segmented silicon (Si) detector, a depleted charge-coupled device (CCD) sensor, and a depleted complementary metal-oxide semiconductor (CMOS) sensor.

19. The apparatus of claim 17, wherein the sensor is a first sensor and the gamma ray probe further comprises: a second sensor proximate to the first sensor.

20. A medical navigation apparatus, comprising:
a housing assembly;
a sensor probe at least partially enclosed within the housing assembly;
a tracking camera at least partially enclosed within the housing assembly, the tracking camera pointing outward from the housing assembly, the tracking camera disposed at a predetermined position and orientation with respect to the probe;
at least one processor and a memory operatively coupled with the tracking camera, the memory having instructions for execution by the at least one processor for:
calculating a spatial position and orientation of the tracking camera with respect to an object based on an image that includes the object; and
computing a spatial position and orientation of the sensor probe; and
associating scanning data from the probe with the computed spatial position and orientation of the sensor probe.

21. The apparatus of claim 20, wherein the sensor probe is selected from the group consisting of a magnetic sensor, an electromagnetic sensor, and a gamma ray detector.

* * * * *